US006992203B2

(12) United States Patent
Trusovs

(10) Patent No.: US 6,992,203 B2
(45) Date of Patent: Jan. 31, 2006

(54) METAL COMPLEXES PRODUCED BY MAILLARD REACTION PRODUCTS

(75) Inventor: Sergejs Trusovs, Ventura, CA (US)

(73) Assignee: JH Biotech, Inc., Ventura, CA (US)

( * ) Notice: Subject to any disclaimer, the term of this patent is extended or adjusted under 35 U.S.C. 154(b) by 201 days.

(21) Appl. No.: 10/605,987

(22) Filed: Nov. 12, 2003

(65) Prior Publication Data

US 2005/0033037 A1 Feb. 10, 2005

Related U.S. Application Data

(60) Provisional application No. 60/425,777, filed on Nov. 13, 2002, provisional application No. 60/457,802, filed on Mar. 26, 2002.

(51) Int. Cl.
C07F 19/00 (2006.01)
C07K 1/00 (2006.01)
(52) U.S. Cl. .......................... 556/50; 556/63; 556/116; 556/134; 556/148; 530/400
(58) Field of Classification Search ................ 530/400; 556/50, 63, 116, 134, 148
See application file for complete search history.

(56) References Cited

U.S. PATENT DOCUMENTS

| | | | | |
|---|---|---|---|---|
| 3,014,026 A | * | 12/1961 | Harry Kroll et al. | 536/55 |
| 3,637,640 A | | 1/1972 | Huber | 260/115 |
| 4,172,072 A | * | 10/1979 | Ashmead | 530/345 |
| 4,216,144 A | * | 8/1980 | Ashmead | 530/345 |
| 4,315,927 A | | 2/1982 | Evans | 514/188 |
| 4,487,766 A | | 12/1984 | Mach | 424/180 |
| 4,599,152 A | | 7/1986 | Ashmead | 205/435 |
| 4,741,900 A | | 5/1988 | Alavarez et al. | 424/85 |
| 4,814,177 A | | 3/1989 | Walsdorf et al. | 424/464 |
| 4,830,716 A | | 5/1989 | Ashmead | 205/457 |
| 5,504,055 A | | 4/1996 | Hsu | 504/121 |
| 5,516,925 A | | 5/1996 | Pedersen et al. | 556/50 |
| 5,698,724 A | * | 12/1997 | Anderson et al. | 556/50 |
| 6,114,379 A | | 9/2000 | Wheelright et al. | 514/492 |
| 6,139,882 A | * | 10/2000 | Ikenaga et al. | 426/74 |
| 6,150,547 A | * | 11/2000 | Sakurai et al. | 556/148 |
| 6,165,378 A | | 12/2000 | Maruno et al. | 252/62.53 |
| 6,426,424 B1 | * | 7/2002 | Ashmead et al. | 556/1 |
| 6,670,494 B1 | * | 12/2003 | Trusovs | 556/49 |
| 6,710,079 B1 | * | 3/2004 | Ashmead et al. | 514/492 |
| 2003/0013772 A1 | | 1/2003 | Murphy et al. | 514/674 |
| 2003/0069172 A1 | * | 4/2003 | Ericson et al. | 514/6 |

OTHER PUBLICATIONS

"Reaction Conditions Influence the Elementary Composition and Metal Chelating Affinity of Nondialyzable Model Maillard Reaction Products"; Wijewickreme, Kitts, Durance; J. Agric. Food Chem., 1997, 45, 4577-4583.

"Mutagenicity of Heated Sugar-Casein Systems: Effect of the Maillard Reaction Brands", C.M.J., Alink, G.M., Van Boekel, A.J.S., Jongen, W.M.F.; J. Agric. Food Chem. 2000, 48, 2271-2275.

"Food browning and Its Prevention: An Overview", M. Friedman, J. Agric. Food Chem. 1996, 44, No. 3, 631-653.

"Relationships between Antioxidant Activity, Color, and Flavor Compounds of Crystal Malt Extracts"; Woffenden; Ames; Chandra; J. Agric. Food Chem. 2001, 49, 5524-5530.

"Antioxidant Activity of Coffee Model Systems"; Charurin, Ames, Dolores Del Castillo; J. Agric. Food Chem. 2002, 50, 3751-3756.

"A Calorimetric Field Test for Metal Complexation in Copper and Zinc Organic Minerals"; Holwerda; Dept. of Chemistry and Biochemistry, Texas Tech University.

J.A. rendleman Jr. and G.E. Inglett: "The influence of Cu2+ in the Maillard reaction", Elsevier Science Publishers, 1990.

B. Fallico and J.M. Ames:"Effect of Hexanal and Iron on Color Development in a Glusoce/Phenylalaning Model Systems", American Chemical Society, 1999.

J. O'Brien and P.A. Morissey, "Metal ion complexion by products of the Millard reaction", Elsevier Science Publishers, 1995.

* cited by examiner

Primary Examiner—Porfirio Nazario-Gonzalez
(74) Attorney, Agent, or Firm—Ralph D. Chabot

(57) ABSTRACT

A method is disclosed for the formation of metal chelates which are able to remain stable in high alkaline environments when compared to metal chelates produced from a reaction with amino acids. The method involves the reaction of sugars, amino groups, and metal components for a sufficient period of time and temperature in a water solution. Additionally, the stability of metal chelates can be enhanced by oxidation of the sugars with an oxidizing agent such as hydrogen peroxide which form an MRP which will react with the metal component to form a more stable metal chelate than if oxidation were not utilized.

11 Claims, No Drawings

200
METAL COMPLEXES PRODUCED BY MAILLARD REACTION PRODUCTS

CROSS REFERENCE TO RELATED APPLICATIONS

This application claims the benefit of provisional application bearing Ser. No. 60/457,802 filed Mar. 26, 2003 which claims the benefit of provisional application bearing Ser. No. 60/425,777 filed Nov. 13, 2002.

BACKGROUND OF INVENTION

Metals chelated by organic ligands are used as an important trace mineral source for humans and animals. Certain metal ions are especially known to be beneficial in stimulating plant growth leading to the production of larger, healthier plants, and increased production of fruits or vegetables. It has become generally accepted that the chelated forms of metals using organic acids are better assimilated by plants, animals, and human beings than are metal salts. Plant, animal and human tissue samples indicate increased metal content when exposed to metal organic acid chelates.

Metal chelates have been produced in the prior art from the reaction of a metal ion (usually in the form of soluble metal salt) with an organic acid or its salt having a mole ratio of one mole of metal to one to three moles of organic acid (depending upon the valency and coordination number of the metal ion) to form coordinate covalent bonds.

Amino and other organic acid chelates can be produced by reacting an organic acid with a metal ion in the form of an oxide, hydroxide or salt. In the prior art, for example, amino acid chelates have generally been made by reacting a metal salt with one or more amino acids, dipeptide, and polypeptide or protein hydrolisate ligands under appropriate conditions to form an amino acid chelate. Metal picolinates can be synthesized by the reaction of a metal salt with picolinic acid salt in an aqueous solution. Calcium or magnesium citrates can be synthesized by the reaction of citric acid with calcium or magnesium oxide, with either an hydroxide or carbonate water suspension. Other carboxylic acids such as hydroxy citric, malic, ascorbic, gluconic, etc. may be used for the preparation of metal salts, complexes and chelates.

A common example is the metal chelate FeEDTA which is produced by reacting the metal salt iron sulfate with an organic acid, ethylenediaminotetraacetic acid (EDTA), or its di or tetra sodium salts.

Patents indicative of the prior art are: U.S. Pat. No. 4,315,927 issued to Evans; U.S. Pat. No. 4,814,177 issued to Waldorf; U.S. Pat. No. 4,830,716 and U.S. Pat. No. 4,599,152 issued to Ashmead; U.S. Pat. No. 5,504,055 issued to Hsu; and U.S. Pat. No. 5,516,925 issued to Pedersen.

Although metal chelates formed by the reaction of free metal ions and chelating agents such as amino acids or EDTA are relatively inexpensive to produce, the one significant drawback to metal chelates formed by this process is that the metal chelate typically hydrolyzes at a pH$\leq$11. Therefore, these metal chelates are not stable in strong alkaline environments.

The prior art has also identified what is termed a Maillard Reaction (MR). The MR occurs nonenzymatically in foods between reducing sugars and available amino groups during thermal processing. ("Reaction Conditions Influence the Elementary Composition and Metal Chelating Affinity of Nondialyzable Model Maillard Reaction Products", Wijewickreme, Kitts, Durance; J. Agric. Food Chem., 1997, 45, 4577–4583).

The MR is an important reaction that occurs in food preparation. The reaction can occur under severe or mild heating conditions and through many complex chemical intermediates, which ultimately lead to the production of brown compounds, known as melanoidins. Melanoidins are known to be non-water soluble.

The formation of MR products (MRPs) is greatly influenced by both the reaction conditions and the sources of the reaction sugars and amino acids. The MR has been extensively studied from various chemical, technological, physical, and toxicological points of view in foods and medicines. Studies have reported that MRPs exhibit antioxidant activity and antimutagenicity ("Mutagenicity of Heated Sugar-Casein Systems: Effect of the Maillard Reaction", Brands, C. M. J., Alink, G. M., Van Boekel, A. J. S., Jongen, W. M. F.; J. Agric. Food Chem. 2000, 48, 2271–2275).

It is important to note that MR is a sequence of natural chemical transformations occurring during food preparation. This reaction leads to the formation of compounds that, because their volatility, influence a food's overall flavor and taste.

The chemistry of the MR is known as a complex series of reactions leading to the formation of a variety of products, including the flavors, aromas and colors considered important in food science today. Despite the very complicated character of the MR, the first step of the interaction between reducing carbohydrates and amino compounds is the reaction of the carbonyl group of a carbohydrate molecule with the amino group of an amino compound. This reaction causes the formation of the first stable molecular product that has in its molecule both amino and carboxyl groups ("Food browning and Its Prevention: An Overview", M. Friedman, J. Agric. Food Chem. 1996, 44, No.3, 631–653).

The main groups of products formed in the course of MR are N-substituted aldosamines, Shiff bases, aldosylamines, ketosamines, diketosamines, deoxysuloses, melanoidins, etc. The chemistry of these compounds is not well known and their formation mechanism remains obscure. In general, a given reaction mixture is a complicated composition of different organic compounds with unknown structures. However, because the starting materials are primarily: a) reducing sugars (i.e., poly hydroxy compounds containing carbonyl groups); and, b) amino groups containing compounds, the final products contain multiple oxygen and nitrogen atoms. As it is known to those skilled in the art, the strongest chelating agents are usually organic ligands having several functional groups in the molecules of oxygen and nitrogen atoms.

For thousands of years the only source of minerals for humans was cooked food. Vitally important minerals such as Zn, Ca, Mg, Mn, Cu, Fe and others were supplied to the bodies of our ancestors not in the form of metal glycinates, nicotinates, lisinates, etc., but from the cooking process utilized in preparing foods.

SUMMARY OF INVENTION

I have discovered a method for producing chelated metals whereby the formed chelated product is more stable in higher alkaline environments than those chelates formed by the direct reaction of amino acids and metal compounds. The chelates according to my method can be formed by using oxidized or non-oxidized sugars and their interaction products with amino compounds.

As was discussed above, a MR is the reaction of carbonyl groups that are present in sugars with the amino group found in amino acids. The MR typically occurs when cooking vegetables containing sugars with the amino groups found in the protein of meats and fish.

In cooking, high heat produces the brown colored compounds, known as melanoidins which are considered one type of MRP. However, I've discovered that other varieties of MRP's can be produced which are more conducive to forming stable metal chelates in high alkaline environments than are melanoidins. What is required is a reaction between carbonyl groups and amino groups which will produce a soluble MRP. Melanoidins are insoluble due to the high temperature required to produce; again which typically occur in the thermal processing of foods.

Two methods are described for forming soluble metal chelates using sugars which are stable in high alkaline environments. The methods described can use metals in different forms. As defined herein, the term "metal component" can be metal salts, metal hydroxides or metal oxides.

Non-Enhanced Maillard Reaction

The first method combines non-oxidized sugars and amino groups in sufficient amounts at atmospheric pressure under controlled temperature conditions to form a MRP. Then a sufficient amount of a metal component is added and the mixture is heated at or below the boiling temperature of water for a sufficient period of time to obtain the formation of a chelated metal. Although heating is used, the heat is significantly less than the high temperature heat (i.e. >350 degrees F.) which is typically used in the thermal processing of food combinations during cooking. The temperature used according to my method is at a level so that none, or only a de minimus amount of insoluble melanoidins are formed.

Enhanced Maillard Reaction

I discovered that by oxidizing sugars, I am able to increase the stability of the produced metal chelates at higher pH than if oxidation was not utilized. It is known in the oxidation of organic compounds, the usual sequence of oxidative transformation of carbon atoms in sugar molecules is: $CH_2OH \rightarrow CHO \rightarrow COOH$.

My process utilizes the principles described in the MR discussed earlier. However, an oxidation step is included to enhance the yield of carbonyl groups in the sugar molecules which then are capable of reacting with the amino acids present leading to an alternative form of MRP. This alternative form of MRP has the characteristic of being capable of forming a more stable metal chelate when reacted with a metal component.

As is well known in the prior art, oxidation is temperature critical. Too low a temperature and the reaction will occur not at all or too slowly. Too high a temperature and the reaction will destroy the sugar molecule. Preferably, the temperature range for oxidation would be between 40 C–80 C. A sufficient amount of hydrogen peroxide would be the preferred component for oxidation but is preferably added slowly to the mixture to control the reaction. However, any component capable of oxidizing sugars to form additional carbonyl groups can be used. Other oxidizing compounds which can be used instead of hydrogen peroxide include hypochlorides, periodites, air, and oxygen. It is to be understood where either air or oxygen is to be used, they would be supplied in gas form and be allowed to bubble through the solution mixture.

The MRP is typically brown in color. When reacted with metal components, metal chelates are produced which are water soluble and will not precipitate at high pH. Test results have indicated chelate stability for products formed from the Non-Enhanced Maillard Reaction to at least pH 12; and, for products formed from the Enhanced Maillard Reaction to at least pH 13.

The ability to use sugars in the metal chelating process is greatly desired because sugars are a less expensive raw material than the commonly used hydroxy carboxylic acids chelating agents. The prior art has not embraced the use of sugars as chelating agents and using sugars provide a natural, inexpensive, and effective alternative to producing chelating agents for the production of chelated metal complexes.

My invention makes possible an effective and inexpensive product for delivering metals such as iron in solution to plants existing in high alkaline environments.

Stable chelates using salts, hydroxides or oxides of Ca, Mg, Mn, Cu, Zn, Co, Cr, K, Fe and other metals of interest can be produced using my method. Sugar sources may include different mono- and disaccharides, dextrose, high fructose corn syrup, starches, maltodextrins, and etc. Amino components may include glycine, lysine, glutamic and other amino acids, dipeptides, polypeptides, protein hydrolizates, milk solids, cream, egg solids, gelatin, whey proteins, etc.

DETAILED DESCRIPTION

Several examples are supposed to illustrate our invention. For all tests unless otherwise specified, the total weight of the chelate formed is substantially the sum of the sugar, amino group and metal.

Iron Maillardate I 6.75 g of glycine, 5.28 g of glucose and 80 ml of water were placed into a beaker provided with a reflux condenser. The mixture was stirred and boiled for 2 hours. Thereafter, 5.1 g of $FeSO_4 \times H_2O$ was added and the mixture was stirred and boiled for an additional 1 hour to obtain chelated iron. Afterwards, the reaction mixture was evaporated on a rotary evaporator under vacuum and then dried and milled. The reaction product (chelate) obtained was in the form of a fine brown powder. The product is water-soluble and has stable chelated iron properties up to at least pH 12.

Iron Maillardate II 6.75 g of glycine, 10.26 g of sucrose, and 80 ml of water were placed into a beaker provided with a reflux condenser. The mixture was stirred and boiled for 2 hours. Thereafter, 5.1 g of $FeSO_4 \times H_2O$ was added to the mixture and stirred and boiled for an additional 1 hour to obtain the formation of chelated iron. Afterwards, the reaction mixture was evaporated on a rotary evaporator under vacuum and then dried and milled. The reaction product (chelate) obtained was in the form of a fine brown powder. The product is water-soluble and has stable chelated iron properties up to at least pH 12.

Iron Maillardate III 6.75 g of glycine, 10.26 g. of sucrose, and 80 ml of water were placed into a beaker provided with a reflux condenser. The mixture was stirred and boiled for 2 hours. Thereafter, 2.57 g of $Fe_2O_3$ was added to the mixture and stirred and boiled for an additional 1 hour to obtain the formation of chelated iron. Afterwards, the reaction mixture was evaporated on a rotary evaporator under vacuum and then dried and milled. The reaction product (chelate) obtained was in the form of a fine brown powder. The product is water-soluble and has stable chelated iron properties up to at least pH 12.

Iron Maillardate IV 2.25 g of glycine, 20.52 g of sucrose, and 80 ml of water were placed into a beaker provided with a reflux condenser. The mixture was stirred and boiled for 2 hours. Thereafter, 5.1 g of $FeSO_4 \times H_2O$ was added to the mixture and stirred and boiled for an additional 1 hour to obtain the formation of chelated iron. Afterwards, the reaction mixture was evaporated on a rotary evaporator under vacuum and then dried and milled. The reaction product (chelate) obtained was in the form of a fine brown powder. The product is water-soluble and has stable chelated iron properties up to at least pH 12.

Copper Maillardate I 6.75 g of glycine, 10.26 g. of sucrose, and 80 ml of water were placed into a beaker provided with a reflux condenser. The mixture was stirred and boiled for 2 hours. Thereafter, 7.1 g. of $CuSO_4 \times 5H_2O$ was added to the mixture and stirred and boiled for an additional 1 hour to obtain the formation of chelated copper. Afterwards, the reaction mixture was evaporated on a rotary evaporator under vacuum and then dried and milled. The reaction product (chelate) obtained was in the form of a fine dark powder. The product is water soluble and has strongly chelated copper complex properties that were proved by the Holwerda test as described in: "A Colorimetric Field Test for Metal Complexation in Copper and Zinc Organic Mineral" by Robert A. Holwerda, Ph.D., Department of Chemistry and Biochemistry, Texas Tech University, Lubbock, Tex. 79409-1061).

Copper Maillardate II 2.25 g of glycine, 20.52 g of sucrose, and 80 ml of water were placed into a beaker provided with a reflux condenser. The mixture was stirred and boiled for 2 hours. Thereafter, 7.1 g. of $CuSO_4 \times 5H_2O$ was added to the mixture and stirred and boiled for an additional 1 hour to obtain the formation of chelated copper. Afterwards, the reaction mixture was evaporated on a rotary evaporator under vacuum and then dried and milled. The reaction product (chelate) obtained was in the form of a fine dark powder. The product is water soluble and has strongly chelated copper complex properties that were proved by the Holwerda test mentioned above.

Zinc Maillardate I 6.75 g of glycine, 5.4 g of glucose, and 80 ml of water were placed into a beaker provided with a reflux condenser. The mixture was stirred and boiled for 2 hours. Thereafter, 2.43 g of ZnO was added to the mixture and stirred and boiled for an additional 1 hour to obtain the formation of chelated zinc. Afterwards, the reaction mixture was evaporated on a rotary evaporator under vacuum and then dried and milled. The reaction product (chelate) obtained was in the form of a fine yellow-brown powder. The product is water-soluble and has strongly chelated zinc complex properties that was proved by the Holwerda test mentioned above.

Synthesis of MRP

The following pair of tests were performed to establish that a larger quantity of soluble metal chelates can be formed by reaction at atmospheric pressure and temperatures at or below the boiling temperature of water as compared to reactions occurring at higher temperature and pressure conditions. In this case, two tests were run with identical quantities, 61.54 g of sucrose, 27 g of glycine, and 23 g water were reacted.

The first test subjected the quantities to approximately 120–125 degrees C. at 2.5 atm for 3 hours in a closed vessel. The reaction product included approximately 25 ml of a dark brown liquid and the remainder of the reaction product was best described as a dark brown rubbery mass. The rubbery mass was cut into small pieces, to increase its surface area and was thereafter boiled in 700 ml of water for 40 min to extract all water soluble constituents from the brown rubbery mass. Following boiling, the mixture was cooled and then filtered. The weight of the insoluble precipitate was 38.1 g. The filtrate was then combined with the 25 ml described above and then evaporated in a rotary vacuum evaporator and dried and milled into a brown powder. The total amount of powder obtained was approximately 48 g. This amount represents a recovery of 56%. Stated a different way, using high temperature and pressure, the amount of water soluble material obtained was 56% of the total solids recovered.

A second test was applied to the same quantities of reactants. However, for this test was performed at atmospheric pressure and at a temperature between 95–98 C for 3 hours. The reaction product was obtained in the form of a dark brown viscous liquid. Since no rubbery mass was obtained as was the case for the first test, only 200 ml was added instead of the 700 ml for the first test. The 200 ml was deemed a sufficient quantity to dilute the viscous liquid and was added directly to the container after the 3 hour period and mixed. After, the liquid mixture was filtered and no precipitate was recovered. The liquid was then evaporated in a rotary vacuum evaporator and dried and milled into a brown powder. The total amount of water soluble powder obtained was approximately 88 g and is designaated as MRP I. This represents an improved recovery of 83% over the method used in the first test.

Zinc Maillardate II 17 g of the MRP I, 4.83 g of $ZnSO_4$, and 80 ml of water were placed into a beaker provided with a reflux condenser. The mixture was stirred and boiled for 2 hours to obtain the formation of chelated zinc. Afterwards, the reaction mixture was evaporated on a rotary evaporator under vacuum and then dried and milled. The reaction product obtained was in the form of a fine yellow-brown powder. The product is water-soluble and has strongly chelated zinc complex properties that was proved by the Holwerda test mentioned above.

Magnesium Maillardate I 6.75 g of glycine, 10.26 g sucrose, and 80 ml of water were placed into a beaker provided with a reflux condenser. The mixture was stirred and boiled for 2 hours. Thereafter, 1.2 g of MgO was added to the mixture and stirred and boiled for an additional 1 hour to obtain the formation of chelated magnesium. Afterwards, the reaction mixture was evaporated on a rotary evaporator under vacuum and then dried and milled. The reaction product obtained was in the form of a fine dark powder. The product is water-soluble and has stable chelated magnesium properties up to at least pH 12.

Chromium Maillardate I 6.75 g of glycine, 10.26 g of sucrose, and 80 ml of water were placed into a beaker provided with a reflux condenser. The mixture was stirred and boiled for 2 hours. Thereafter, 7.99 g of $CrCl_3 \times 6H_2O$ was added to the mixture and stirred and boiled for an additional 1 hour to obtain the formation of chelated chromium. Afterwards, the reaction mixture was evaporated on a rotary evaporator under vacuum and then dried and milled. The reaction product obtained was in the form of a fine brown powder. The product is water-soluble and has stable chelated chromium properties up to at least pH 12.

Manganese Maillardate I 6.75 g of glycine, 10.26 g of sucrose and 80 ml of water were placed into a beaker provided with a reflux condenser. The mixture was stirred and boiled for 2 hours. Thereafter, 4.53 g of $MnSO_4$ was added to the mixture and stirred and boiled for an additional 1 hour to obtain the formation of chelated manganese. Afterwards, the reaction mixture was evaporated on a rotary evaporator under vacuum and then dried and milled. The reaction product obtained was in the form of a fine dark powder. The product is water-soluble and has stable chelated manganese properties up to at least pH 12.

The following are examples of the Enhanced Maillard Reaction by oxidizing sugars.

Iron Maillardate V 5.1 g $FeSO_4H_2O$, 10.26 g sucrose and 80 ml water were placed into a beaker provided with a reflux condenser. The mixture was continuously stirred and heated in a water bath for 10–15 min up to 80 C. Thereafter, 5 ml 30% hydrogen peroxide was added to the reaction solution. Afterwards, 2.25 g glycine was added and the reaction mixture was heated in a boiling water bath for 1 hour to obtain the formation of chelated iron. Afterwards, the reaction mixture was placed in a rotary evaporator under the vacuum and then dried and thereafter milled. The reaction product (chelate) obtained was in the form of a fine brown powder. The product is water-soluble, has stable chelated iron properties up to at least pH 13.

Iron Maillardate VI 14 g $Fe(OH)_3$, 25 g sucrose and 46 ml water were placed into a beaker provided with a reflux condenser. The mixture was continuously stirred and heated in a water bath up to 80 C and 10 ml of 30% hydrogen peroxide was added slowly over the next 40 min to the reaction mixture. Afterwards, 4.7 g glycine was added and the reaction mixture was continuously stirred and heated in a boiling water bath for an additional 1 hour to obtain the formation of chelated iron. The reaction product (chelate) was a dark green viscous solution, has stable chelated iron properties up to at least pH 13.

Iron Maillardate VII 15.39 g lactose, a catalytic amount of 0.2 g $Fe(OH)_3$ and 40 ml water were placed into a beaker provided with a reflux condenser. The mixture was continuously stirred and heated in a water bath at up to 80 C and 5 ml of 30% hydrogen peroxide was added slowly over the next 20 min to the system. Thereafter, 2.25 g glycine as added to the reaction product and stirred and heated for an additional 1 hour to obtain the formation of MP. Thereafter, 3.01 g of $Fe(OH)_3$ was added to the solution and continuously stirred and heated for an additional 1.5 hours to obtain the formation of chelated iron. Next, the reaction mixture was placed in a rotary evaporator under the vacuum and then dried and thereafter milled. The reaction product (chelate) obtained was in the form of a fine brown powder. The product is water-soluble and has stable chelated iron properties up to at least pH 13.

Iron Maillardate VII 3.21 g of $Fe(OH)_3$, 25 g molasses and 30 g of hydrolyzed whey protein were placed into a beaker provided with a reflux condenser. The mixture was continuously stirred and heated in a water bath up to 80 C. 7 ml 30% hydrogen peroxide was added slowly over 30 min and the system was continuously stirred and heated at 80 C for an additional 2 hours to obtain the formation of chelated iron. Afterwards, the reaction mixture was placed in a rotary evaporator under vacuum and dried and thereafter milled. The reaction product (chelate) obtained was in the form of a fine brown powder. The product is water-soluble and has stable chelated iron properties up to at least pH 13.

Copper Maillardate III 10.26 g sucrose, a catalytic amount of 0.2 g $CuSO_45H_2O$ and 40 ml water were placed into a beaker provided with a reflux condenser. The mixture was continuously stirred and heated in a water bath up to 80 C and 6 ml 30% hydrogen peroxide was added slowly over 15 min and then continuously stirred and heated at up to 80 C for an additional 2 hours to obtain formation of the chelating agent. Afterwards, 7.3 g of $CuSO_45H_2O$ was added to the reaction product and continuously stirred and heated for an additional 1 hour to obtain the formation of chelated copper. Thereafter, the reaction mixture was placed in a rotary evaporator under the vacuum, dried and then milled. The reaction product (chelate) obtained was in the form of a fine dark powder. The product is water-soluble and has strongly chelated copper complex properties confirmed by the Holwerda test as described in: "A Colorimetric Field Test for Metal Complexation in Copper and Zinc Organic Minerals." Robert A. Holwerda, Ph.D., Department of Chemistry and Biochemistry, Texas Tech University, Lubbock, Tex.

Copper Maillardate IV 2.25 g glycine, 20.52 g sucrose, and 80 ml water were placed into a beaker provided with a reflux condenser. The mixture was continuously stirred and heated up to 80 C for 2 hours. Thereafter, 7.1 g $CuSO_45H_2O$ was added to the reaction product and 6 ml 30% hydrogen peroxide was added slowly over 15 min and then stirred and heated at up to 80 C for an additional 1 hour to obtain the formation of chelated copper. Afterwards, the reaction mixture was placed in a rotary evaporator under the vacuum, dried and then milled. The reaction product (chelate) was obtained in the form of a fine dark powder. The product is water soluble and has strongly chelated copper complex properties that were confirmed by the Holwerda test mentioned above.

Zinc Maillardate III 6.25 g ZnO, 39.6 g sucrose, 0.3 g $CuSO_45H_2O$ used as a catalyst, and 24 ml water were placed into a beaker provided with a reflux condenser. The mixture was continuously stirred and heated up to 80 C in a water bath and 30 ml 30% hydrogen peroxide was added slowly over 60 min at up to 80 C. The reaction mixture was continuously stirred and heated at up to 80 C for an additional 1 hour, then cooled and filtered. Afterwards, 2.89 g glycine was added to the filtrate and stirred and heated at up to 80 C for 1 hour. Afterwards, the reaction mixture was placed in a rotary evaporator under vacuum, dried and then milled. The reaction product (chelate) obtained was in the form of a fine yellow-brown powder. The product is water-soluble, stable in the solution at high pH and has strongly chelated zinc complex properties that were confirmed by the Holwerda test mentioned above.

Synthesis of Solubilized MRP using Oxidized Sugars

This test combined in a beaker, 61.54 g sucrose with 50 ml water and 46 ml of a 30% hydrogen peroxide solution in the presence of a catalytic amount (0.3 g) of $CuSO_4×5H_2O$. The combination was mixed for 30 min at 85 C. Thereafter, 27 g glycine was added to the oxidized sucrose solution, stirred, and heated in a water bath for 2 hours at between 95–98 C. The reaction product was obtained in the form of a brown viscous liquid. 100 ml water was added for dilution. After, the liquid mixture was filtered and 2.6 g of precipitate was recovered. The filtrate was then evaporated in a rotary vacuum evaporator and dried and milled into a brown powder. The total amount of water soluble powder obtained was approximately 84 g and is designated as MRP II.

Zinc Maillardate IV 17 g MRP II, 4.83 g $ZnSO_4$ and 80 ml water were placed into a beaker provided with a reflux condenser. The mixture was continuously stirred and heated in a water bath up to 80 C for 1 hour to obtain the formation of chelated zinc. Afterwards, the reaction mixture was placed in a rotary evaporator under the vacuum, dried and then milled. The reaction product (chelate) obtained was in the form of a fine brown powder. The product is water-soluble and has strongly chelated zinc complex properties that were confirmed by the Holwerda test mentioned above.

Magnesium Maillardate II 10.26 g sucrose, 1.2 g MgO and 80 ml water were placed into a beaker provided with a reflux condenser. The mixture was continuously stirred, heated in a water bath up to 80 C and oxidized by 7 ml 30% hydrogen peroxide as described earlier. Then 2.25 g glycine was added to the reaction product and stirred and boiled for an additional 1 hour to obtain the formation of chelated magnesium. Afterwards, the reaction mixture was placed in a rotary evaporator under vacuum dried and then milled. The reaction product (chelate) obtained was in the form of a fine dark powder. The product is water-soluble and has stable chelated magnesium properties up to at least pH 13.

Chromium Maillardate II 6.75 g of glycine, 10.26 g sucrose, and 80 ml water were placed into a beaker provided with a reflux condenser. The mixture was continuously stirred and heated up to 80 C and 6 ml 30% hydrogen peroxide was added slowly over 15 min. Thereafter, 7.99 g $CrCl_3 6H_2O$ was added to the reaction product and stirred and heated for an additional 1 hour at up to 80 C to obtain the formation of chelated chromium. Afterwards, the reaction mixture was placed in rotary evaporator under vacuum, dried and then milled. The reaction product (chelate) obtained was in the form of a fine brown powder. The product is water-soluble and has stable chelated chromium properties up to at least pH 13.

Manganese Maillardate II 3.37 g glycine, 8.1 g glucose and 35 ml water were placed into a beaker provided with a reflux condenser. The mixture was continuously stirred and heated in a water bath up to 80 C and 5 ml 30% hydrogen peroxide was added slowly over 15 min. Thereafter, 6.04 g $MnSO_4$ were added to the reaction product and stirred and heated for an additional 1 hour to obtain the formation of chelated manganese. Afterwards, the reaction mixture was placed in a rotary evaporator under vacuum, dried and then milled. The reaction product (chelate) obtained was in the form of a fine dark powder. The product is water-soluble and has stable chelated manganese properties up to at least pH 13.

What is claimed is:

1. A method for producing a metal chelate comprising the steps of:
   providing a sufficient amount of at least one amino component;
   providing a sufficient amount of at least one sugar component;
   providing a sufficient amount of at least one metal component; and,
   mixing said sufficient amounts of said amino component, sugar component, and metal salt component with water for a sufficient time and at a sufficient temperature to form a soluble metal chelate containing solution where the chelate is a Maillard Reaction Product.

2. The method of claim 1 further comprising the steps of evaporating the soluble metal chelate containing solution; thereafter drying to form a dried metal chelate; and, milling to form a powder of dried metal chelate.

3. The method of claim 1 where:
   said amino component is selected from the group consisting of glycine, lysine, glutamic and other amino acids, dipeptides, polypeptides, protein hydrolizates, milk solids, cream, egg solids, gelatin, and whey proteins;
   said sugar component is selected from the group consisting of sucrose, disaccharides, dextrose, high fructose corn syrup, starches, maltodextrins; and,
   said metal component is selected from the group consisting of salts, hydroxides and oxides of calcium, manganese, magnesium, copper, zinc, cobalt, chromium, potassium, and iron.

4. The method of claim 2 where:
   said amino component is selected from the group consisting of glycine, lysine, glutamic and other amino acids, dipeptides, polypeptides, protein hydrolizates, milk solids, cream, egg solids, gelatin, and whey proteins;
   said sugar component is selected from the group consisting of sucrose, disaccharides, dextrose, high fructose corn syrup, starches, maltodextrins; and,
   said metal component is selected from the group consisting of salts, hydroxides and oxides of calcium, manganese, magnesium, copper, zinc, cobalt, chromium, potassium, and iron.

5. A method for producing a metal chelate comprising the steps of:
   providing a sufficient amount of at least one amino component;
   providing a sufficient amount of at least one sugar component;
   providing a sufficient amount of at least one metal component;
   providing a sufficient amount of at least one oxidizing compound; and,
   mixing said sufficient amounts of amino component, sugar component, oxidizing compound and metal component with water for a sufficient time and temperature so that said sugar present is substantially oxidized thereby forming metal chelates in a soluble metal chelate containing solution.

6. The method of claim 5 further comprising the steps of evaporating the soluble metal chelate containing solution; thereafter drying to form a dried metal chelate; and, milling to form a powder of dried metal chelate.

7. The method of claim 5 where:
   said amino component is selected from the group consisting of glycine, lysine, glutamic and other amino acids, dipeptides, polypeptides, protein hydrolizates, milk solids, cream, egg solids, gelatin, and whey proteins;
   said sugar component is selected from the group consisting of sucrose, disaccharides, dextrose, high fructose corn syrup, starches, maltodextrins;
   said metal component is selected from the group consisting of salts, hydroxides and oxides of calcium, manganese, magnesium, copper, zinc, cobalt, chromium, potassium, and iron; and,
   said oxidizing compound is selected from the group consisting of hydrogen peroxide, hypochlorides, periodites, air, and oxygen.

8. The method of claim 6 where:
   said amino component is selected from the group consisting of glycine, lysine, glutamic and other amino acids, dipeptides, polypeptides, protein hydrolizates, milk solids, cream, egg solids, gelatin, and whey proteins;
   said sugar component is selected from the group consisting of sucrose, disaccharides, dextrose, high fructose corn syrup, starches, maltodextrins;

said metal component is selected from the group consisting of salts, hydroxides and oxides of calcium, manganese, magnesium, copper, zinc, cobalt, chromium, potassium, and iron; and, said oxidizing compound is selected from the group consisting of hydrogen peroxide, hypochlorides, periodites, air, and oxygen.

9. A method for producing a metal chelate comprising the steps of:

providing an amino component selected from the group consisting of: glycine, lysine, glutamic and other amino acids, dipeptides, polypeptides, protein hydrolizates, milk solids, cream, egg solids, gelatin, and whey proteins;

providing a sugar component selected from the group consisting of: sucrose, disaccharides, dextrose, high fructose corn syrup, starches, maltodextrins;

providing a metal component selected from the group consisting of salts, hydroxides and oxides of calcium, manganese, magnesium, copper, zinc, cobalt, chromium, potassium, and iron;

combining said amino component and said sugar component in water to form a solution and mix at atmospheric pressure for a sufficient time and temperature to form a solubilized Maillard Reaction Product solution;

thereafter, adding said metal component to said Maillard Reaction Product solution and mix at atmospheric pressure for a sufficient time and temperature to form a solubilized metal chelate solution; and, evaporating said solubilized metal chelate solution to yield a metal chelate, drying said metal chelate to form a dried metal chelate; and, milling to form a metal chelate powder.

10. The method of claim 9 where a sufficient amount of an oxidizing compound is added to said solution containing said amino component and said sugar component to form a solubilized Maillard Reaction Product solution.

11. The method of claim 10 where said oxidizing compound is selected from the group consisting of hydrogen peroxide, hypochlorides, periodites, air, and oxygen.

* * * * *